United States Patent [19]

Lueders et al.

[11] Patent Number: 4,847,368

[45] Date of Patent: Jul. 11, 1989

[54] METHOD OF MANUFACTURING ALKYLOLIGOGLYCOSIDES

[75] Inventors: Harald Lueders, Recklinghausen; Peter Hofmann, Marl, both of Fed. Rep. of Germany

[73] Assignee: Huels Aktiengesellschaft, Marl, Fed. Rep. of Germany

[21] Appl. No.: 191,408

[22] Filed: May 9, 1988

[30] Foreign Application Priority Data

Sep. 5, 1987 [DE] Fed. Rep. of Germany ....... 3729844

[51] Int. Cl.$^4$ ...................... C07G 15/00; C07G 3/00; C07H 15/04
[52] U.S. Cl. ................................. 536/18.6; 536/120; 536/4.1
[58] Field of Search ........................ 536/18.6, 4.1, 120

[56] References Cited

U.S. PATENT DOCUMENTS

| | | | |
|---|---|---|---|
| 3,715,402 | 2/1973 | Louvar | 536/4.0 |
| 4,683,297 | 7/1987 | Yanami | 536/4.1 |
| 4,704,453 | 11/1987 | Lorenz | 536/4.1 |
| 4,739,043 | 4/1988 | DeFaye | 536/18.6 |

*Primary Examiner*—Johnnie R. Brown
*Assistant Examiner*—Pamela C. Webber
*Attorney, Agent, or Firm*—Oblon, Spivak, McClelland, Maier & Neustadt

[57] ABSTRACT

A method of manufacturing alkyloligoglycosides. Alkyloligoglycosides and alkylglycosides having alkyl groups with 8 to 24 carbon atoms, which are of interest in home economics and in the cosmetics industry, can be manufactured by glycosidation and transglycosidation. Light-colored alkyloligoglycosides and alkylglycosides are manufactured from saccharides and alcohols by glycosidation and transglycosidation with the addition of polar polymeric complex-forming agents, and by bleaching of the final products with peroxides.

12 Claims, No Drawings

METHOD OF MANUFACTURING ALKYLOLIGOGLYCOSIDES

BACKGROUND OF THE INVENTION

1. Field of the Invention

The invention relates to a method which, with the aid of complex-forming agents, enables the production of alkyloligoglycosides and alkylglycosides having alkyl groups with 8 to 24 carbon atoms.

2. Discussion of the Background

Alkyloligoglycosides and alkylglycosides with alkyl groups having 8 to 24 carbon atoms can be prepared partially or completely from many types of raw materials. These alkyloligoglycosides and alkylglycosides are becoming increasingly important, due to their interesting surface-active properties combined with very good biodegradability. For use in the home economics and cosmetics sectors, these products must meet stringent esthetic requirements. Therefore methods are sought by which alkyloligoglycosides and alkylglycosides can be produced in aqueous solutions, and which are transparent and have an attractive color.

In the production of alkyloligoglycosides and alkylglycosides with long-chain alkyl groups, one generally first employs glycosidation of saccharides with short-chain alcohols, to produce alkyloligoglycosides and alkylglycosides with alkyl groups having 1 to 6 carbon atoms. These intermediate products are then converted to the desired alkyloligoglycosides and alkylglycosides by transglycosidation, at elevated temperature. However, the products thus produced are dark in color.

According to European Pat. No. 165,721, the color of such products can be improved by multistage bleaching with hydrogen peroxide, and can be stabilized by addition of compounds which liberate sulfur dioxide. The lightening effect is only of short duration in the absence of sulfur dioxide.

According to European Pat. No. 77,167, reducing agents such as hypophosphorous acid or sulfurous acid can be added in the reaction of alcohols with aldoses or ketoses. The color of the alkylglycosides is thereby improved. Small amounts of reducing agents are effective with this method only if the process is carried out with the exclusion of oxygen.

Preventive measures are also known. Thus, according to European Pat. No. 102,558, one obtains $C_3$ to $C_5$ alkylglucosides of improved color if the glucosidation is carried out in the presence of an alkali salt of a boron acid.

In preparing long-chain alkylsaccharides, according to U.S. Pat. No. 4,465,828, color improvement can be obtained with the aid of the hydroxypolycarboxylic acids such as citric acid, tartaric acid, and malic acid. However, the improvement achieved in light-permeability of the solutions is inadequate for many applications.

According to U.S. Pat. No. 4,483,979, coloring factors can be extracted from alkylpolysaccharides. This costly procedure requires anhydrous polar solvents. In addition, part of the alkylpolysaccharides are extracted in the process, along with the colorants.

According to European Pat. No. 99,183, water-containing polysaccharides can be reacted with alcohols to form light-colored alkylglycoside solutions. However, the method requires cosolvents such as methanol and acetone, and leads to reaction mixtures with a high content of unconverted saccharide.

European Pat. No. 132,064 discloses that alkylglycoside solutions can be neutralized, after completion of the reaction, by means of alkali alcoholates or alkali salts of carboxylic acids. In this connection, sodium methoxide leads to only a slightly more than 50% reduction in absorption in the visible range, in comparison to sodium hydroxide.

The known methods of producing alkyloligoglycosides of improved color are cumbersome, require expensive reagents, or else do not lead to the desired color qualities.

SUMMARY OF THE INVENTION

Accordingly, one object of the present invention is to provide a simplified and more efficacious method of producing light-colored alkyloligoglycosides and alkylglycosides having alkyl groups with 8 to 24 carbon atoms.

This and other objects which will become apparent from the following specification have been achieved by the present method of manufacturing alkyloligoglycosides and alkylglycosides having $C_{8-24}$ alkyl groups from saccharides and alcohols, comprising the steps of:

(i) reacting one or more saccharides with a $C_{8-24}$ alcohol at an elevated temperature and in the presence of an acid catalyst and a complex-forming agent, said agent comprising a polar polymer having a HLB-value (hydrophile-lipophile balance) of 10–20, to produce a product solution containing the alkyloligoglycosides and alkylglycosides;

(ii) separating the alkyloligoglycosides and alkylglycosides from the product solution; and (iii) bleaching the alkyloligoglycosides and alkylglycosides with a peroxide compound.

DETAILED DESCRIPTION OF THE PREFERRED EMBODIMENTS

The light-colored alkyloligoglycosides and alkylglycosides of the present invention are prepared by the present method in which:

(1) one adds a polar polymer with a HLB-value (hydrophile-lipophile balance) of 10–20 during the glycosidation and/or transglycosidation to form the desired products;

(2) the products of the glycosidation or transglycosidation, in solution in an alcohol or alcohols, may be treated with an adsorption agent; and (3) the products produced, or aqueous preparations of the products, are bleached with peroxide compounds, after distillation to remove the alcohols.

To prepare the alkyloligoglycosides and alkylglycosides having alkyl groups with 8 to 24 carbon atoms, one first carries out a glycosidation, for which the starting compounds are hexoses, pentoses, oligomeric saccharides, or mixtures of these. Examples of such starting compounds include glucose, mannose, galactose, sorbose, fructose, xylose, arabinose, ribose, lyxose, lactose, and maltose. Commercially available water-containing starch hydrolyzate syrups may be used, such as dextrose syrup, glucose syrup, or maltose syrup. The products may also contain oligosaccharides. Preferably the starting materials used are glucose preparates such as dextrose or dextrose syrups.

Short-chain primary or secondary alcohols with 1 to 6 carbon atoms are used for the glycosidation, preferably, n-butanol.

The products of the glycosidation are the starting compounds for the transglycosidation, namely alkylglycosides and alkyloligoglycosides having alkyl groups with 1 to 6 carbon atoms, and with mean oligomerization numbers of 1 to about 6. Preferably these products are butylglucosides and butyloligoglucosides.

These products are reacted with $C_8$ to $C_{24}$ alcohols in the transglycosidation reaction. For example, surface active alcohols originating from natural products, in particular such alcohols as are produced in the hydrogenation of fatty acids or fatty acid derivatives, may be used, or entirely synthetic Ziegler alcohols, oxo alcohols, or mixtures of these may be used. They may contain branched or unbranched alkyl groups. Preferably the alcohols contain 8 to 20 carbon atoms.

The transglycosidation is generally carried out at 80°–140° C., preferably at 90°–120° C. It may be carried out discontinuously or continuously and is terminated after a (mean) reaction time of about 0.5–4 hr. The total time for the glycosidation and transglycosidation is about 1.5–8 hr.

The products of the transglycosidation are alkyloligoglycosides and alkylglycosides having 8 to 24 carbon atoms. They have a mean oligomerization number of 1 to about 10. Preferred products are alkyloligoglycosides and alkylglycosides having 8 to 24 carbon atoms which are manufactured according to the inventive method.

Products having an iodine color number of <30 when in 50% aqueous solution are designated "light-colored".

The alcohols used in the glycosidation and transglycosidation may also serve as solvents for the starting compounds and the products.

As catalysts for the glycosidation and transglycosidation, strong mineral acids, organic acids, or strongly acid ion exchangers may be used. For example, sulfuric acid or p-toluenesulfonic acid may be used.

The polar polymers used as complex-forming agents are characterized by their HLB values. A high HLB value indicates a high polarity. Polymers are preferred which have HLB values of about 10–20.

Preferred complexing agents are polyetherdiols with molar oxygen:carbon ratios of 1:2 to 1:3 having a $M_n$ range of about 200 to about 10,000,000 or cyclic ethers with molar oxygen:carbon ratios of 1:2 to 1:3 or polymers of vinylpyrrolindone having a $M_w$ range of about 10,000 to about 10,000,000. Polyethylene glycols and crown ethers (for an example, see Table 1 below) are especially preferred. The complex-forming agents are added in the amount of 0.001 to 10 wt.%, preferably 0.01–1 wt% based on the weight of the saccharide used.

The products of the glycosidation and transglycosidation may be treated with adsorption agents. For this purpose, preferably 0.01–10 wt.% activated carbon (based on the weight of the solution) is stirred into the products at 10°–140° C., and at the end of the treatment the activated carbon is filtered out.

After distillation and removal of the long-chain alcohols, the residue may be treated with water to form a pumpable solution. The residue or an aqueous preparation of it is then bleached with a peroxide compound or solution thereof, e.g., hydrogen peroxide, peracetic acid, perbenzoic acid, or peroxy disulfuric acid, at 50°–100° C., preferably 70°–90° C. The preferred bleaching agent is hydrogen peroxide, preferably used in concentrations of about 0.05–5 wt.% based on the products of transglycosidation.

The inventive method enables production of light-colored alkyloligoglycosides and alkylglycosides having alkyl groups with 8 to 24 carbon atoms, with low expenditures for apparatus and chemicals. The method may be carried out discontinuously or continuously. It is technically a simple matter to provide metered addition of the complex-forming agents.

The method provides products with very good color quality, which are suitable for numerous applications in which esthetic qualities are a factor as well as surface active properties and biodegradability.

The color improvement is substantial, with an effect greater than would be expected by the additive effects of the individual techniques.

The complexing agents are used in such small amounts that they do not detract from the surface active properties of the products, and therefore they do not need to be removed from the products. They generally can improve the detergent properties of the products, as well.

The general method for manufacturing the light-colored products is as follows: Starting with a saccharide or a saccharide syrup, one adds 0.5–10 mol short-chain alcohols per mol of saccharide units, 2–200 milliequivalents (meq) acid per kg of alcohol, and the complex-forming agents. The glycosidation is then conducted at 80°–130° C., with distillation to remove water.

The resulting glycosidation products may be purified with activated carbon before adding the additional materials for the transglycosidation. These additional materials are namely 0.5–10 mol long-chain alcohols per mol of saccharide units, 2–200 meq acid per kg of alcohol, and preferably fresh complex-forming agents. The total amount of complex-forming agents should be in the range 0.001–10 wt.% based on the amount of saccharides used. The transglycosidation is carried out at 80°–140° C., preferably at reduced pressure, with distillation to remove the short-chain alcohols. The products are surface active alkyloligoglycosides and alkylglycosides, dissolved in long-chain alcohols.

After neutralization, a treatment with activated carbon may be carried out. It is also possible to distill off the long-chain alcohols under vacuum at this point. The residue of the distillation is preferably dissolved in water and then bleached with hydrogen peroxide at about 70° C. Then after evaporation, one obtains the desired light-colored surface-active products.

Other features of the invention will become apparent in the course of the following descriptions of exemplary embodiments which are given for illustration of the invention and are not intended to be limiting thereof.

EXAMPLES

Example 1

In a 250 ml flask fitted with stirrer, reflux condenser, and Dean-Stark trap for removing water, 50 g butylglucoside, 87.5 g n-butanol, 40 g 70% aqueous dextrose syrup, 1.6 ml 2N butanolic sulfuric acid, and 32 mg PEG 400 (polyethylene glycol with $M_n = 400$) were boiled under stirring, reflux, and water separation, for 3 hr at 700 mbar, with the temperature being kept within the range 95°–105° C. Thereafter the Fehling test for aldehydes was negative.

Then an additional 87.5 g n-butanol, 40 g 70% aqueous dextrose syrup, 1.1 ml 2N butanolic sulfuric acid, and 32 mg PEG 400 were added, followed by boiling another 3 hr at 700 mbar and 95°-105° C., with water separation. The Fehling test was then again negative.

2.5 g activated carbon powder was added to the glycosidation products (dissolved in n-butanol) thus produced. The mixture was stirred 30 min at room temperature, and then was filtered.

228 g filtrate, 400 g Alfol® 1012 (see Table 1, below), 7.3 ml 2N butanolic sulfuric acid, and 100 mg PEG 400 were stirred at 30 mbar and 110° C. in a 1-liter flask with distillation condensor and receiving vessel, wherewith n-butanol was distilled off. After 2 hr the transglycosidation was ended.

The reaction mixture was neutralized with 2N sodium hydroxide and then was buffered with 100 mg sodium bicarbonate. The mixture was stirred 1 hr at 80° C. and then was subjected to evaporation in a rotary evaporator, under oil pump vacuum, with a bath temperature of 150° C.

The residue, which was essentially an alkyloligoglycoside having alkyl groups with 10 to 14 carbon atoms and an oligomerization number of 1.2, was converted to a 50% solution with an equal weight of water.

100 g of this solution was bleached with 3.3 ml 30% hydrogen peroxide solution, for 1 hr at 70° C. Thereafter the solution had an iodine color number of 5. After evaporation of the bleached solution under aspirator vacuum, the product obtained had a very light beige color.

Examples 2 to 6

The procedure was as in Example 1, except that various complex-forming agents (in the same amounts) were employed, and in some cases different long-chain alcohols were employed. The results are summarized in Table 1.

TABLE 1

| Example No. | Complexing Agent | Long-chain alcohol | ICN# |
|---|---|---|---|
| 2 | 12-Crown-4(R)* | Alfol(R) 1012** | 5–7 |
| 3 | PEG ($M_n$ = 1,550) | C.f.a. 12/14*** | 15 |
| 4 | PEG ($M_n$ = 1.2 × 10$^6$) | C.f.a. 12/14 | 10 |
| 5 | Polyvinylpyrrolidone K-value = 90, $M_w$ = 360,000) | C.f.a. 12/14 | 7–10 |

*12-Crown-4(R) = A crown ether, cyclo-1,4,7,10-tetraoxadodecanone, supplied by the firm Aldrich-Chemie, of D-7924 Steinheim;
**Alfol(R) 1012 = An alcohol mixture, having the approximate composition 85% n-decanol, 8.5% n-dodecanol, and 6.5% n-tetradecanol, supplied by the firm Condea, of D-2212 Brunsbuettel;
***C.f.a. 12/14 = Coconut fatty alcohol 12/14 = An alcohol mixture, having the approximate composition 1% n-decanol, 72% n-dodecanol, 25% n-tetradecanol, and 1% hexadecanol.
ICN = Iodine carbon number.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of manufacturing alkyloligoglycosides and alkylglycosides having $C_{8-24}$ alkyl groups from saccharides and alcohols, comprising the steps of:
   (i) reacting one or more saccharides with a $C_{1-6}$ alcohol to prepare a $C_{1-6}$ alkylglycoside or alkyloligoglycoside;
   (ii) reacting said $C_{1-6}$ alkylglycoside or alkyloligoglycoside with a $C_{8-24}$ alcohol at an elevated temperature and in the presence of an acid catalyst, wherein a complex-forming agent, said agent comprising a polar polymer having a HLB-value (hydrophilelipophile balance) of 10–20 is present during at least one of steps (i) and (ii), to produce a product solution containing said $C_{8-24}$ alkyloligoglycoside or alkylglycoside;
   (iii) separating said $C_{8-24}$ alkyloligoglycoside or alkylglycoside from said product solution; and
   (iv) bleaching said $C_{8-24}$ alkyloligoglycoside or alkylglycoside with a peroxide compound.

2. The method of claim 1, wherein said complex-forming agent is a polyether diol having a molar oxygen:carbon ratio of 1:2–1:3.

3. The method of claim 1, wherein said complex-forming agent is a cyclic ether having a molar oxygen:carbon ratio of 1:2–1:3.

4. The method of claim 1, wherein said complex-forming agent is a vinylpyrrolidone polymer.

5. The method of claim 1, wherein said complex-forming agent is added in amounts of about 0.001–10 wt.% based on the weight of said saccharide.

6. The method of claim 5, wherein said complex-forming agent is added in an amount from 0.01–1 wt.%.

7. The method of claim 1, wherein said peroxide compound is selected from the group consisting of hydrogen peroxide, peracetic acid, perbenzoic and peroxy disulfuric acid.

8. The method of claim 1, wherein said peroxide compound is used in concentrations of about 0.05–5 wt.% based on said alkyloligoglycosides and alkylglycosides.

9. The process of claim 1, wherein said peroxide compound is hydrogen peroxide used in amounts from about 0.05–5 wt.% based on the weight of said alkyloligoglycosides and alkylglycosides.

10. The method of claim 1, further comprising:
    treating said product solution at 10°–140° C. with 0.01–10 wt.% of an adsorption agent based on the weight of said solution.

11. The method of claim 10, wherein said adsorption agent is activated carbon.

12. The method of claim 1, wherein said reacting step is conducted at a temperature of 80°–140° C. for 0.5–4 hours.

* * * * *

UNITED STATES PATENT AND TRADEMARK OFFICE
CERTIFICATE OF CORRECTION

PATENT NO. : 4,847,368
DATED : July 11, 1989
INVENTOR(S) : Lueders et al.

It is certified that error appears in the above-identified patent and that said Letters Patent is hereby corrected as shown below:

In Column 6, line 55, after "step" insert --(ii)--

Signed and Sealed this

Twenty-fourth Day of July, 1990

Attest:

HARRY F. MANBECK, JR.

*Attesting Officer*  *Commissioner of Patents and Trademarks*